United States Patent [19]

Harman, III et al.

[11] 4,411,764

[45] Oct. 25, 1983

[54] HYDROGEN ION INTERFERENT REDUCTION SYSTEM FOR ION SELECTIVE ELECTRODES

[75] Inventors: John N. Harman, III, Pasadena; Robert H. Jones, Irvine, both of Calif.

[73] Assignee: Beckman Instruments, Inc., Fullerton, Calif.

[21] Appl. No.: 321,297

[22] Filed: Nov. 13, 1981

[51] Int. Cl.³ ............................................. G01N 27/28
[52] U.S. Cl. ................................................... 204/411
[58] Field of Search ................. 204/195 R, 1 A, 1 H, 204/195 G, 195 M, 411; 324/425, 438

[56] References Cited

U.S. PATENT DOCUMENTS

| | | | |
|---|---|---|---|
| 3,718,556 | 2/1973 | Rohrback | 204/149 |
| 3,839,162 | 10/1974 | Ammer | 204/1 T |
| 3,941,665 | 3/1976 | Eckfeldt et al. | 204/195 R X |
| 4,011,297 | 3/1977 | Nyman et al. | 423/24 |
| 4,052,285 | 10/1977 | Dobson | 204/195 G |
| 4,058,437 | 11/1977 | Young | 204/1 T |
| 4,131,428 | 12/1978 | Diggens | 23/230 R |

*Primary Examiner*—G. L. Kaplan
*Attorney, Agent, or Firm*—R. J. Steinmeyer; P. R. Harder; E. C. Jason

[57] ABSTRACT

An ion activity or concentration analyzer including an ion selective electrode, a reference electrode and a flow-through electrolytic cell. A sample liquid enclosure conducts a flow of an aqueous sample past the anode and cathode electrodes of an electrolytic cell that is polarized to generate hydrogen and hydroxyl ions. The ion selective and reference electrodes are so positioned, with respect to the cathode electrode, that the hydroxyl ion concentration is increased in the vicinity thereof. This increased hydroxyl ion concentration causes a reduction in the hydrogen ion concentration and thereby substantially eliminates the interfering effect of hydrogen ions on the operation of the ion selective and reference electrodes.

15 Claims, 4 Drawing Figures

U.S. Patent    Oct. 25, 1983    Sheet 1 of 2    4,411,764
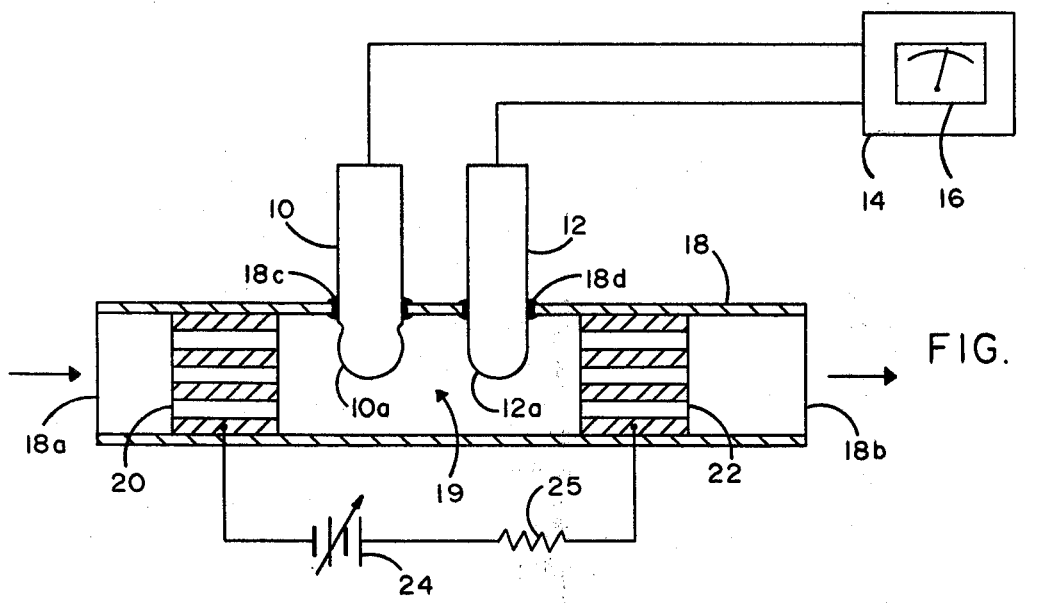
FIG. 1
$$(1)\ 4H_2O + 4e^- = 2H_2 + 4OH^-$$
$$(2)\ 2H_2O - 4e^- = O_2 + 4H^+$$
$$(3)\ O_2 + 2H_2O + 4e^- = 4OH^-$$
$$(4)\ 2H_2O - 4e^- = O_2 + 4H^+$$
FIG. 1b
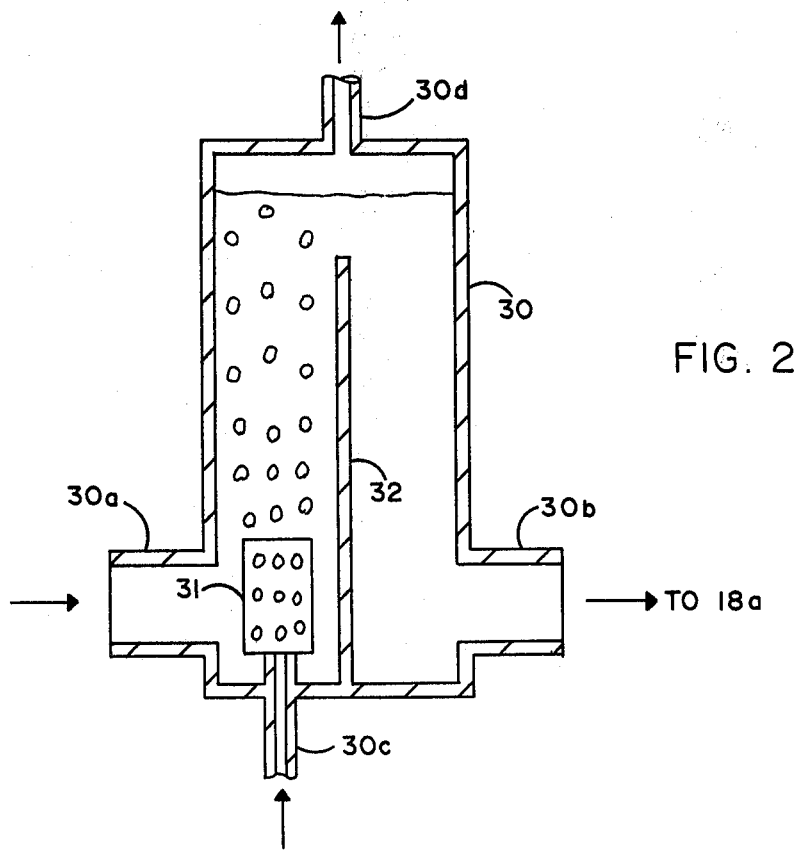
FIG. 2

HYDROGEN ION INTERFERENT REDUCTION SYSTEM FOR ION SELECTIVE ELECTRODES

BACKGROUND OF THE INVENTION

In process control applications in which the activity or concentration of cationic species such as sodium, potassium or ammonium ions must be carefully monitored, ion selective electrodes, such as glass electrodes, provide a convenient means for providing the desired information. In electrical power generating stations, for example, electrodes that are sensitive to sodium ion concentration can provide a continuous indication of the effectiveness of the ion exchange beds through which the boiler feed water is passed prior to being supplied to the boilers. In such use, an increase in the electrode output reading from a value on the order of one part per billion to a value of several parts per billion may be used as an indication that the ion exchange capability of the ion exchange bed is approaching exhaustion. This allows the ion exchange bed to be removed from service for regeneration prior to the time that increased levels of dissolved salts can damage the interior of the boiler system.

One serious limitation on the usefulness of ion selective electrodes is the limited ability thereof to discriminate between the cation of interest and other small cations. Sodium ion sensitive electrodes, for example, are known to respond to some degree to ammonium and potassium ions. Particularly troublesome, however, is the sensitivity of sodium ion sensitive electrodes to hydrogen ions. This is not only because of the greater interferent effect of hydrogen ions, but also because hydrogen ion concentration bears no meaningful relationship to the total dissolved salt content. As a result, in the absence of precautions for eliminating the effect of hydrogen ions, the output reading of a sodium ion sensitive electrode could be substantially greater than the actual concentration of sodium ions, causing unnecessary servicing of ion exchange beds.

Prior to the present invention, the above-described problem has been dealt with in one of two ways. One of these ways has involved the addition of compounds that increased the alkalinity of the sample. An example of this approach is shown and described in U.S. Pat. No. 3,941,665, issued on Mar. 2, 1976 in the name of Eckfeldt et al.

Another approach to solving the problem of cationic interference involves the division of the sample stream into first and second parts, each of which is applied to a respective ion selective electrode. By passing one of the parts through an ion exchanger of known effectiveness in removing the cation of interest, the ion selective electrode that is exposed to that part in effect provides a signal indicative of the concentration of interfering cations. By then taking the difference between the output signals of the two ion selective electrodes, the effect of interfering cations is made to cancel, leaving an interference free signal that is proportional to the concentration of the cation of interest. An example of this approach is shown and described in U.S. Pat. No. 3,839,162, issued on Oct. 1, 1974 in the name of Ammer.

The problem with the first of the above-described solutions to the interference problem is that the addition of pH raising compounds such as methylamines chemically contaminates the sample. This problem is particularly severe in applications in which the sample liquid flows in a closed system. The feed water of a power generating boiler, for example, may be vaporized, condensed and recirculated many times during its useful life. As a result, any compounds that are added to the flow will, over a period of time, accumulate to undesirable levels. Another problem with the use of such compounds is that they are toxic to humans. Such problems, of course, are in addition to the costs of providing the compound and the cost of the apparatus for delivering the same.

The problem with the second of the above-described solutions to the interference problem is the high cost of providing and maintaining the ion exchange beds through which the sample is processed. Another disadvantage of this approach is that it creates a risk of serious errors, since there is no effective way of determining when the ion exchange beds cease to effectively remove the ions to which they are targeted. As a result, the user is faced with the choice of regenerating the ion exchangers on a precautionary basis, i.e., while they are still usable, or waiting until the beds are known to be exhausted and thereby risking the failures that may occur before the exhaustion of the ion exchanger is discovered.

SUMMARY OF THE INVENTION

In accordance with the present invention, there is provided an improved ion concentration analyzer which is substantially free of hydrogen ion interference and which has none of the disadvantages of the interference eliminating schemes used in prior analyzers. In the preferred embodiment, the analyzer includes an ion selective glass measuring electrode and a reference electrode which are enclosed in a flow-through electrolytic cell. This electrolytic cell electrically generates a local excess concentration of hydroxyl ions in the vicinity of the measuring and reference electrodes, and thereby greatly reduces the hydrogen ion concentration in that vicinity. This, in turn, substantially eliminates the interferent effect of hydrogen ions on the measuring and reference electrodes. Optionally, the present invention may include structures for introducing dissolved gases into the liquid flowing through the electrolytic cell and thereby changing the voltage and current required to generate the desired hydroxyl ions.

In accordance with an important feature of the present invention, the anode and cathode electrodes of the electrolytic cell are so positioned that, in spite of the simultaneous generation of equal numbers of hydroxyl and hydrogen ions, only hydroxyl ions are concentrated in the vicinity of the measuring and reference electrodes. This is accomplished by utilizing the flow of the sample liquid through the cell to prevent hydrogen ions from migrating toward the vicinity of the measuring and reference electrodes. In one embodiment, for example, the measuring and reference electrodes are positioned downstream of the cathode electrode of the electrolytic cell (the hydroxyl ion generating electrode) and upstream of the anode electrode thereof (the hydrogen ion generating electrode). In another embodiment, the anode and cathode electrodes of the electrolytic cell are located in respective branches of a T-shaped flow enclosure, with the measuring and reference electrodes located downstream of the cathode electrode.

In the preferred embodiment, the electrolytic cell is arranged to produce sufficient hydroxyl ions to reduce the hydrogen ion concentration to a level at least approximately 100 times less than that of the cation of interest. Much smaller concentration ratios, such as 1,000 times less, are, however, beneficial and easily obtainable through the use of the present invention. Naturally, even relatively small reductions in hydrogen ion concentration, e.g., a reduction by a factor of 10, will be beneficial although there is little reason to use such small reductions when much greater reductions are easily achieved.

An important advantage of the present invention is that it completely eliminates the need to add contaminating chemicals to the sample liquid. This, in turn, allows the concentration analyzer of the invention to be used in closed systems for long periods on a substantially maintenance-free basis. A related advantage is that the use of an electrolytic cell has no lasting effect on the chemical composition of sample liquid. This is because the desired hydroxyl ion concentration exists only in the vicinity of the measuring and reference electrodes and is eliminated by the recombination of hydroxyl and hydrogen ions after the sample liquid leaves the vicinity of the analyzer. Thus, the present invention provides a hydrogen ion interferent correction apparatus which is noncontaminating and nonexhaustable.

Another advantage of the present invention is that it produces its effect without the need for a closed loop control system. One reason is that sodium ion measuring electrodes are insensitive to hydroxyl ions. As a result, the hydroxyl ion concentration can fluctuate over relatively wide limits without a significant adverse effect on the ability of the analyzer to provide the desired hydrogen ion interference elimination. This, in turn, allows the circuitry used in practicing the invention to have a simple, inexpensive open-loop design. Thus, in spite of its advantages, the cost of the present invention is comparable to or less than the cost of prior systems.

DESCRIPTION OF THE DRAWINGS

FIG. 1 is a cross-sectional view of one embodiment of a concentration analyzer that is constructed in accordance with the present invention, FIG. 1b sets forth pairs of electrolytic reactions that may be used in practicing the present invention, FIG. 2 is a cross-sectional view of an accessory that may be used with the embodiment of FIG. 1.

DESCRIPTION OF THE PREFERRED EMBODIMENTS

Figure 3:
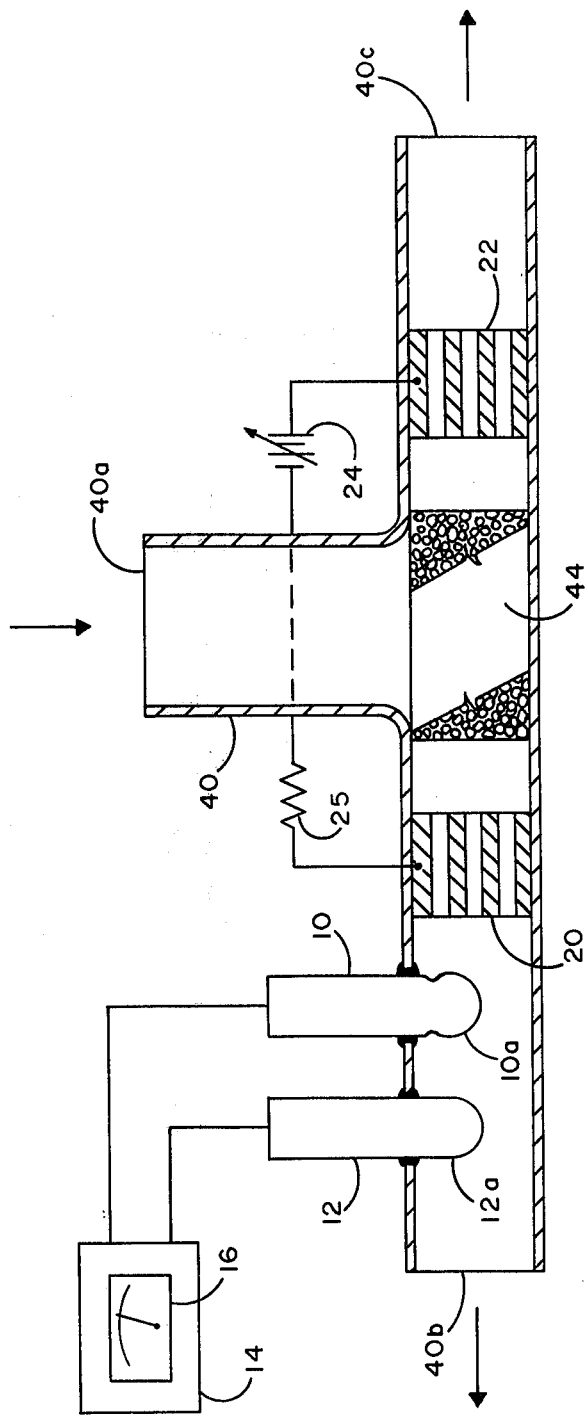
FIG. 3 is a cross-sectional view of an alternative embodiment of the present invention.

Referring to FIG. 1, there is shown an ion concentration analyzer including an ion selective measuring electrode 10, a reference electrode 12 and a high input impedance potentiometric measuring unit 14 having an output display 16. Measuring electrode 10 is preferably a glass electrode that is sensitive to a particular cationic species such as sodium, potassium or ammonium ions and may be of a conventional type. Reference electrode 12 serves to establish the potential with respect to which the output voltage of measuring electrode 10 is measured and may also be of a conventional type, although the reference electrode described in U.S. Pat. No. 4,002,547 is preferred because of the absence of a leak structure therein. Equivalently, a combination electrode having both an ion sensitive portion and a reference portion may be used in place of separate electrodes 10 and 12. Finally, potentiometric measuring unit 14 may be of any suitable type such as, for example, that sold by Beckman Instruments, Inc. under Model No. 942.

To the end that measuring electrode 10 and reference electrode 12 may be exposed to only a negligible concentration of hydrogen ions, the active ends 10a and 12a thereof are located within an electrically nonconductive sample flow enclosure 18 having an inlet 18a and outlet 18b. In applications in which the quantity of the liquid to be tested is large, enclosure 18 may be included as part of a branch line through which only a small fraction of the liquid to be measured flows. On the other hand, if the quantity of the liquid to be measured is small, the entire flow thereof may be directed through enclosure 18. In order to avoid contamination, enclosure 18 is preferably constructed from a material which is nonreactive with any of the components of the liquid flowing therethrough.

In the event that the sample flow passage through enclosure 18 has a square or rectangular cross-section, electrodes 10 and 12 may be sealably mounted in enclosure 18 by suitable grommets 18c and 18d, as shown in FIG. 1. Alternatively, if an enclosure having a sample flow passage with a circular cross section is utilized, other suitable mounting and sealing structures, such as those including T-connectors and O-rings, may be utilized in place of grommets 18c and 18d. In general, any mounting and sealing arrangement which is capable of withstanding exposure to the sample liquid at its operating temperature and pressure is suitable for practicing the present invention.

To the end that the hydrogen ion concentration may be reduced in the vicinity of the active ends of measuring electrode 10 and reference electrode 12, enclosure 18 is provided with an electrolytic cell including a cathode electrode 20 and an anode electrode 22, the latter electrodes being supplied with a suitable d.c. operating voltage from a variable d.c. source 24.

While the size and shape of cathode electrode 20 and anode electrode 22 are not critical, it is preferred that these electrodes have a configuration such that liquid cannot flow through enclosure 18 without passing close to the surface of each electrode. One suitable configuration, comprising a solid cylindrical body having a plurality of holes drilled parallel to the axis thereof, is shown in cross-sectional form for each of electrodes 20 and 22 in FIG. 1. Other configurations, such as coiled strips of metal screen or solid metal, are also usable, however, provided only that their composition is such that they do not react chemically with substances that are dissolved in the sample liquid.

In accordance with the present invention, electrodes 10 and 12 are so positioned with respect to cathode 20 and anode 22 that sample liquid flowing through enclosure 18 encounters electrodes 10 and 12 only after flowing past cathode 20, and encounters anode 22 only after leaving the vicinity of electrodes 10 and 12. In the embodiment of FIG. 1, this is accomplished by causing the sample liquid to flow into inlet 18a and out of outlet 18b.

The foregoing relationships assure that the hydroxyl ions produced at cathode electrode 20 increase the pH of the sample liquid in the vicinity of electrodes 10 and 12 before mixing with and being neutralized by the hydrogen ions produced at anode electrode 22. As a result of the increased hydroxyl ion concentration in the vicinity of electrodes 10 and 12, i.e., region 19, the hydrogen ion concentration is correspondingly reduced, resulting in the substantial elimination of the interfering effect of hydrogen ions on the operation of electrodes 10 and 12. In this connection it will be understood that the rate of flow of the sample liquid through enclosure 18 should be sufficiently high that hydrogen ions produced at anode 22 cannot migrate upstream, under the influence of the electrostatic field established by source 24, fast enough to destroy the desired local increase in hydroxyl ion concentration within region 19.

More particularly, referring to FIG. 1b, equations (1) and (2) describe the reactions that occur at cathode electrode 20 and anode electrode 22, respectively. From equation (1) it will be seen that the reaction at cathode electrode 20 involves the reduction of four molecules of water and in the production of four hydroxyl ions and two hydrogen molecules. Simultaneously, the reaction at anode electrode 22 involves the oxidation of two molecules of water and in the production of four hydrogen ions and one molecule of oxygen.

Because, as previously described, the rate of flow of the sample liquid is sufficiently high that no significant number of hydrogen ions can migrate upstream from anode electrode 22 into region 19, hydroxyl ions will accumulate in that region, forming a hydroxyl ion "shadow" downstream of cathode 20. A similar ionic shadow, comprising a local concentration of hydrogen ions, also tends to form downstream of anode 22. The latter concentration is, however, quickly neutralized by hydroxyl ions entering from region 19, thereby restoring the electrical neutrality of the sample liquid. Thus, the action of electrodes 20 and 22 has no lasting effect on the pH or the ionic content of the liquid flowing through enclosure 18.

In view of the foregoing, it will be seen that, by producing a local excess hydroxyl ion concentration in the immediate vicinity of the active ends of electrode 10 and 12, enclosure 18 and the electrolytic cell including electrodes 20 and 22 and source 24 effectively serve as an electrically powered hydrogen ion interferent reactor.

In spite of the fact that measuring and reference electrodes 10 and 12 are located between cathode 20 and anode 22, the electric field gradient between the latter has no significant effect on the operation of the former, provided that two conditions are met. One condition is that source 24 should provide a relatively constant, voltage to electrodes 20 and 22. This constancy of voltage assures that, after the effect of the electric field between electrodes 20 and 22 on electrodes 10 and 12 has been taken into account during the calibration of instrument 14, it may be discounted since it has the same effect on each reading. The other condition is that the dielectric constant of the sample liquid must be relatively constant. Because the present invention contemplates aqueous sample liquids, and because water has an extremely high dielectric constant, this condition is easily met.

In applications in which the electrical conductivity of the sample liquid is relatively high, the electrolytic reactions set forth in equations (1) and (2) will proceed even though source 24 provides a relatively low voltage. In other applications, such as boiler feed water, in which the sample liquid is relatively pure water, the conductivity will be relatively low. One manner of dealing with such low conductivity liquids is to adjust supply 24 to provide a relatively higher voltage. Alternatively, there may be used a set of reactions that are based on the presence of a dissolved oxygen in the sample liquid. One such set of reactions includes the cathode and anode reactions set forth in equations (3) and (4) of FIG. 1b.

The potential necessary to sustain the reaction of equation (3) is less than the potential required to sustain the reaction of equation (1). This, in turn, allows the voltage necessary to drive the reactions of equations (3) and (4) to be less than that necessary to drive the reactions of equations (1) and (2). Thus, the reactions of equations (3) and (4) may be preferable to those of equations (1) and (2) when a sample liquid of low conductivity is involved.

If the reactions of equations (3) and (4) are used, and the sample liquid does not already contain a sufficient quantity of dissolved oxygen, the dissolved oxygen level may be increased by any suitable means, such as pumping filtered air through the sample liquid upstream of cathode electrode 20. One apparatus that may be used for this purpose is shown in FIG. 2. As shown in FIG. 2, this apparatus may include a housing 30 having an inlet 30a, an outlet 30b and an internal partition 32. During the time that the sample liquid is flowing toward the top of partition 32, air may be pumped therethrough from an inlet 30c, the excess (undissolved) air being removed through an outlet 30d. In order to maximize the mixing of air and water, the air entering inlet 30c may be pumped into the sample liquid through a porous diffuser element 31.

One particularly interesting feature of equations (3) and (4) is that the oxygen molecules that are consumed at cathode 20 are regenerated at anode 22. As a result, if the sample liquid is a part of a closed system which has, or can be made to have, sufficient dissolved oxygen to support the reactions of equations (3) and (4), these reactions may be used in practicing the present invention without continuous use of the oxygen dissolving apparatus of FIG. 2. This is because the dissolved oxygen molecules can in effect be reused, their inclusion as a part of hydroxyl ions within region 19 of enclosure 18 being only temporary.

It will be understood that other electrolytic reactions may be used in practicing the embodiment of the invention shown in FIG. 1. The presence (or introduction) of both dissolved oxygen and dissolved hydrogen, for example, allows the use of a still lower voltage from source 24. Because these gases may be introduced in the manner shown in FIG. 2, either from gas storage tanks or from a suitable auxiliary electrolytic cell, embodiments based on the use of both dissolved oxygen and dissolved hydrogen will not be described in detail herein.

Referring to FIG. 3, there is shown an alternative embodiment of the present invention. The embodiment of FIG. 3 is in many respects similar to that of FIG. 1, like functioning parts being similarly numbered. The embodiment of FIG. 3 differs from that of FIG. 1, however, in that measuring electrode 10 and reference electrode 12 are not located between anode 22 and cathode 20. Instead, electrodes 10 and 12 are located, with cathode 20, in a first outlet arm 40b of a T-shaped enclosure 40 having an inlet arm 40a and first and second outlet arms 40b and 40c. Anode 22 is located in second outlet arm 40c of T-shaped enclosure 40. This configuration causes sample liquid entering inlet 40a to divide in two, one half of the liquid flowing to the left past cathode 20 and the other half flowing to the right past anode 22. As a result, the hydroxyl ions produced at cathode 20 are confined to the region downstream thereof, i.e., the vicinity of electrodes 10 and 12, while the hydrogen ions produced at anode 22 are confined to the region downstream of that electrode. Thus, the embodiment of FIG. 2 produces an ion separation and local hydroxyl ion concentration effect which is similar to that described previously in connection with the embodiment of FIG. 1.

One advantage of using the embodiment of FIG. 3 is that it places measuring and reference electrodes 10 and 12 in a region of lower electric field intensity, thereby reducing the importance of the previously mentioned source voltage constancy and contancy of the dielectric constant of the sample liquid. Another advantage is that, by increasing the physical separation of the hydroxyl and hydrogen ion concentrations, the ability of oppositely charge ions to migrate toward one another, against the current, is reduced.

In using the embodiment of FIG. 3, it is preferred that the half of the sample liquid which flows out of outlet 40b be eventually remixed with the half of the sample liquid which flows out of outlet 40c. One reason that this is desirable is that it allows the recombination of the hydrogen and hydroxyl ions and thereby restores the electrical neutrality of the sample liquid after passage through enclosure 40. This recombination is also desirable because it prevents electrostatic forces within enclosure 40 from rising to excessive levels.

Because turbulence may result from the division of sample liquid at the junction of T-shaped enclosure 40, it may be desirable to provide a flow-straightener element 44 in the vicinity of that junction. The elimination of this turbulence, in turn, will eliminate the effect of dynamic flow conditions, such as eddies, which might otherwise produce transient effects on the operation of measuring and reference electrodes 10 and 12. It will be understood that neither the presence of flow-straightener 44, nor the location of electrodes 10 and 12 remotely from anode electrode 22, adversely affects the previously described operation of the present invention.

In view of the foregoing, it will be seen that an ion concentration analyzer constructed in accordance with the present invention not only substantially eliminates the effect of hydrogen ions as an interfering species, but also accomplishes this result without using compounds which contaminate the sample liquid or which must be periodically replenished. In addition, it will be seen that the present invention is suitable both for use both as an integral part of newly constructed ion concentration analyzers and as an accessory to retrofit existing ion concentration analyzers.

What is claimed is:

1. In an analyzer of the type having an ion selective electrode that is adapted to measure the activity of sodium, potassium or ammonium ions and a reference electrode, the improvement comprising:
   (a) an anode electrode,
   (b) a cathode electrode,
   (c) an enclosure for directing a flow of an aqueous sample past the anode and the cathode electrodes,
   (d) means for applying between the anode and cathode electrodes a voltage sufficient to cause the generation of hydroxyl ions at the cathode electrode,
   (e) means for positioning the ion selective electrode and the reference electrode in a region having a local excess hydroxyl ion concentration.

2. An analyzer as set forth in claim 1 in which hydrogen ions are generated at the anode electrode, and in which said hydroxyl and hydrogen ions are allowed to recombine after leaving the vicinity of the anode and cathode electrodes.

3. An analyzer as set forth in claim 1 in which the ion selective and reference electrodes are located between the anode and cathode electrodes and in which the aqueous sample flows from the cathode to the anode.

4. An analyzer as set forth in claim 1 in which the enclosure includes an inlet and first and second outlets, and in which the anode and cathode electrodes are located in respective outlet passages.

5. An analyzer as set forth in claim 1 in which the ion selective and reference electrodes are located in the hydroxyl ion shadow of the cathode electrode.

6. An analyzer as set forth in claim 1 including means for dissolving an oxygen containing gas in the aqueous sample before the latter comes into contact with the cathode electrode.

7. An analyzer as set forth in claim 6 in which the means for dissolving the oxygen containing gas comprises a pump arranged to pump air into the aqueous sample.

8. An analyzer as set forth in claim 1 including a source of oxygen and hydrogen and means for dissolving said oxygen and hydrogen in the aqueous sample.

9. An analyzer as set forth in claim 8 in which said source is an auxiliary electrolytic cell.

10. In an interferent reactor for eliminating the interferent effect of hydrogen ions in an analyzer which is adapted to measure the activity of a monovalent cation, in combination,
   (a) an anode electrode,
   (b) a cathode electrode,
   (c) an enclosure for directing a flow of an aqueous sample past the anode and cathode electrodes,
   (d) means for applying between the anode and cathode electrodes a voltage sufficient to cause hydroxyl ions to be generated at the cathode electrode,
   (e) an ion selective electrode that is responsive to the activity of monovalent cations in the aqueous sample,
   (f) a reference electrode,
   (g) means for postioning the ion selective and reference electrodes between the anode and cathode electrodes,
   (h) said aqueous sample flowing in the direction from the cathode to the anode.

11. The reactor of claim 10 including means for pumping an oxygen containing gas through the aqueous sample to dissolve oxygen therein.

12. The reactor of claim 10 including a source of oxygen and hydrogen and means for dissolving said oxygen and hydrogen in the aqueous sample.

13. In an interferent reactor for eliminating the interferent effect of hydrogen ions in an analyzer which is adapted to measure the activity of a monovalent cation, in combination,
   (a) an anode electrode,
   (b) a cathode electrode,
   (c) an enclosure for directing a flow of an aqueous sample past the anode and cathode electrodes, said enclosure having an inlet passage and first and second outlet passages, said cathode and anode electrodes being located in respective outlet passages,
   (d) means for applying between the anode and cathode electrodes a voltage sufficient to cause hydroxyl ions to be generated at the cathode electrode, (e) an ion selective electrode that is responsive to the activity of monovalent cations in the aqueous sample, (f) a reference electrode, and (g) means for positioning the ion selective and reference electrodes downstream of the cathode electrode.

14. The reactor of claim 13 including means for pumping an oxygen containing gas through the aqueous sample to dissolve oxygen therein.

15. The reactor of claim 13 including a source of oxygen and hydrogen and means for dissolving said oxygen and hydrogen in the aqueous sample.

* * * * *